United States Patent [19]
Liquido et al.

[11] Patent Number: 5,728,394
[45] Date of Patent: Mar. 17, 1998

[54] PESTICIDE COMPOSITION AND METHOD FOR CONTROLLING THE ORIENTAL FRUIT FLY

[75] Inventors: Nicanor J. Liquido; Roy T. Cunningham, both of Hilo, Hi.; James R. Heitz, Starkville, Miss.; John P. Spencer, Honolulu, Hi.

[73] Assignee: Photodye International, Inc., Linthicum, Md.

[21] Appl. No.: 414,402

[22] Filed: Mar. 31, 1995

Related U.S. Application Data

[63] Continuation-in-part of Ser. No. 353,726, Dec. 12, 1994, abandoned.

[51] Int. Cl.$^6$ .................................................. A01N 25/00
[52] U.S. Cl. ................................. 424/405; 424/84
[58] Field of Search ........................... 424/405, 84, 43

[56] References Cited

U.S. PATENT DOCUMENTS

| | | | |
|---|---|---|---|
| 4,320,140 | 3/1982 | Crounse et al. | 424/405 |
| 4,647,578 | 3/1987 | Crounse et al. | 514/454 |
| 4,764,366 | 8/1988 | McGovern et al. | 424/84 |
| 4,855,133 | 8/1989 | Kamei et al. | 424/84 |
| 4,877,607 | 10/1989 | McGovern et al. | 424/84 |
| 4,891,217 | 1/1990 | McGovern et al. | 424/84 |

OTHER PUBLICATIONS

J. R. Heitz, "Development of Photoactivated Compounds as Pesticides," *Light Activated Pesticides,* J. R. Heitz and K. R. Downum (eds.), American Chemical Society Symposium Series 339, American Chemical Society, Washington, D.C. (1987) pp. 1–21.

J. E. Fondren, Jr. and J. R. Heitz, "Dye–Sensitized House Fly Toxicity Produced as a Function of Variable Light Sources," *Environmental Entomology* 8:432–436 (1979).

J. E. Fondren, Jr. and J. R. Heitz, "Xanthene Dye Induced Toxicity in the Adult Face Fly, *Musca autumnalis,*" *Environmental Entomology* 7:843–846 (1978).

M. F. Callaham, J. R. Broome, O. H. Lindig, and J. R. Heitz, "Dye–sensitized Photooxidation Reactions in the Boll Weevil, *Anthonomous grandis,*" *Environmental Entomology* 4:837–841 (1975).

S. L. Clement, R. S. Schmidt, G. Szatmari–Goodman, and E. Levine, "Activity of Xanthene Dyes Against Black Cutworm Larvae," *Journal of Economic Entomology* 73:390–392 (1980).

M. F. Callaham, L. A. Lewis, M. E. Holloman, J. R. Broome, and J. R. Heitz, "Inhibition of the Acetylcholinesterase from the Imported Fire Ant, *Solenopsis Richteri* (Forel) by Dye–Sensitized Photooxidation," *Comp. Biochem. Physiol.* 51:123–128 (1975).

J. R. Broome, M. F. Callaham, and J. R. Heitz, "Xanthene Dye–sensitized Photooxidation in the Black Imported Fire Ant, *Solenopsis richteri,*" *Environmental Entomology* 4:883–886 (1975).

J. E. Fondren, Jr. and J. R. Heitz, "Light Intensity as a Critical Parameter in the Dye–Sensitized Photooxidation of the House Fly, *Musca domestica,*" *Environmental Entomology* 7:891–894 (1978).

J. R. Heitz, "Xanthene Dyes as Pesticides," *Insecticide Mode of Action,* Coast, J.R., (ed.), Academic Press, New York, (1982), pp. 429–459.

(List continued on next page.)

*Primary Examiner*—Raj Bawa
*Attorney, Agent, or Firm*—Leonard Bloom

[57] ABSTRACT

A composition and method for eradicating or suppressing a population of Mediterranean fruit flies or oriental fruit flies which introduces substantially minimal safety risks to humans, agriculture and nontargeted living creatures includes: providing an insecticide composition which includes at least one photoactive dye which is preferably a mixture of Phloxine B and uranine; causing the composition to be ingested by the targeted fruit fly population by spraying or providing the insecticide at a location where the fruit flies feed; and whereby ingestion of the photoactive dye component of the composition by a Mediterranean fruit fly or oriental fruit fly causes a toxic quantity of photons to penetrate within the body of the fly.

3 Claims, 9 Drawing Sheets

OTHER PUBLICATIONS

G. Balasubramaniam, E. V. Abraham, S. Vijayaraghavan, T. R. Subramaniam, T. Santhanaraman, and C. R. Gunasekaran, "Use of Male-annihilation Technique in the Control of the Oriental Fruit Fly, *Dacus dorsalis* Hendel," *Indian Journal of Agricultural Science* 42:975–977 (1972).

R. T. Cunningham, "Male Annihilation," In: *World Crop Pests*, vol. 3B., *Fruit Flies, Their Biology, Natural Enemies and Control*, A. S. Robinson and G. Hooper (Eds.), Elsevier Science Publishers, Amsterdam, The Netherlands (1989) pp. 345–351.

R. T. Cunningham and D. Y. Suda, "Male Annihilation of the Oriental Fruit Fly, *Dacus dorsalis* Hendel (Diptera: Tephritidae): A New Thickener and Extender for Methyl Eugenol Formulations," *Journal of Economic Entomology* 78:503–504 (1985).

R. T. Cunningham and D. Y. Suda, "Male Annihilation Through Mass-trapping of Male Flies with Methyleugenol to Reduce Infestation of Oriental Fruit Fly (Diptera: Tephritidae) Larvae in Papaya," *Journal of Economic Entomology* 79:1580–1582 (1986).

R. T. Cunningham, D. L. Chambers, and A. G. Forbes, "Oriental Fruit Fly: Thickened Formulations of Methyl Eugenol in Spot Applications for Male Annihilation," *Journal of Economic Entomology* 68:861–863 (1975).

R. T. Cunningham, L. F. Steiner, and K. Ohinata, "Field Tests of Thickened Sprays for Methyl Eugenol Potentially Useful in Male-annihilation Programs Against Oriental Fruit Flies," *Journal of Economic Entomology* 65:556–559 (1972).

J. Koyama, T. Teruya, and K. Tanaka, "Eradication of the Oriental Fruit Fly (Diptera: Tephritidae) from the Okinawa Islands by a Male Annihilation Method," *Journal of Economic Entomology* 77:468–472 (1984).

L. F. Steiner, and R. K. S. Lee, "Large-area Tests of a Male Annihilation Method for Oriental Fruit Fly Control," *Journal of Economic Entomology* 48:311–317 (1955).

L. F. Steiner, W. C. Mitchell, E. J. Harris, T. T. Kozuma, and M. S. Fujimoto, "Oriental Fruit Fly Eradication by Male Annihilation," *Journal of Economic Entomology* 58:961–964 (1965).

L. F. Steiner, W. G. Hart, E. J. Harris, R. T. Cunningham, K. Ohinata, and D. C. Kamakahi, "Eradication of the Oriental Fruit Fly from the Mariana Islands by the Methods of Male Annihilation and Sterile Insect Release," *Journal of Economic Entomology* 63:131–135 (1970).

PESTICIDE COMPOSITION AND METHOD FOR CONTROLLING THE ORIENTAL FRUIT FLY

This is a continuation-in-part of application Ser. No. 08/353,726, filed Dec. 12, 1994 now abandoned.

BACKGROUND OF THE INVENTION

The fruit flies of the family Tephritidae include several species that are major pests of agriculture throughout the world and that represent a serious threat to U.S. agriculture. The U.S. Department of Agriculture (USDA), Animal and Plant Health Inspection Service (APHIS), in cooperation with other Federal and State organizations, has conducted a number of programs to eradicate some species of fruit flies when these insects have been introduced. These programs generally have employed an integrated pest management approach to eradication. Many recent programs have involved application of malathion bait spray to effectively lower fly populations in the infested area followed by release of sterile flies. Aerial applications of the bait spray over populated areas to control infestations of fruit flies have been controversial. Concerns about adverse health effects from exposure to malathion bait spray have been raised by residents of treated neighborhoods. The currently used malathion bait system for control of Mediterranean fruit flies contains as the main ingredients, Nu-Lure (acid hydrolyzed protein) as an attractant food bait and the contact insecticide, malathion. This system has a bad public perception, damages paint finishes on cars, and, because of the high concentration of insecticides (10–20%) in the bait to ensure temporal stability, this insecticide is extremely detrimental to beneficial insects that may contact the bait surface or be exposed to volatile fumes after application. The United States government has mandated that certain currently listed pesticides, such as malathion, should have a more restricted use pattern. The Environmental Protection Agency has specifically requested that safer pesticides be developed for use in the agricultural sector.

SUMMARY OF THE INVENTION

In the quest for these aforementioned safer pesticides, it has been unexpectedly discovered that dye-sensitized photoactive substances can be effectively utilized as the active ingredient in insecticides for use in a bait station or as bait spray component which target Mediterranean fruit flies and many other tephritid fruit flies. The preferred photoactive dye for these purposes is a halogenated xanthene such as phloxine B or a mixture of a halogenated xanthene and uranine. Other known xanthene dyes which could be used include erythrosin B and rose bengal. These dyes are more fully described in the U.S. patents to Crounse and Heitz, U.S. Pat. No. 4,647,578 and U.S. Pat. No. 4,320,140, the subject matter of which is incorporated herein by reference. When employing halogenated xanthene dyes, light activated toxicity is especially marked with respect to Mediterranean fruit flies and oriental fruit flies. The photoactive dye ingredient of the present invention is effective due to the release of light induced free radical molecules within the body of the insect which has ingested the composition containing the dye. Due to its small proportionate body mass, the dose of light is fatal to the insect.

Although being extremely toxic with respect to the targeted Mediterranean fruit fly or oriental fruit fly, the preferred dyes of the instant invention are non-toxic to humans, most mammals, and nontargeted insects. This is a substantial advance in the industry, as prior art pesticides which were adapted for the purpose of controlling fruit fly populations, namely malathion, have posed health risks to humans. Because malathion is highly penetrating and invades cells very quickly upon contact, malathion is highly potent as a poison, both to insects and nontargeted species. The present invention, on the other hand, is directed to an active ingredient which is toxic to the targeted Mediterranean or oriental fruit fly, not due to cell penetration, but rather due to exposure to a quantity of light which is fatal to the fly. The effect of the same quantity of exposure by a human or other mammal would be negligible. In this regard, the compound phloxine B (2',4',5',7'-tetrabromo-4,5,6,7-tetrachlorofluorescein) has been consumed by humans for decades. It is registered as D & C Red No. 28 as a drug and cosmetic additive and has been included into such commercially available products as Pepto Bismol. In fact, the intrinsic toxicity of malathion is 62.5 times greater than that of phloxine B as measured by acute $LD_{50}$ in rats.

Additionally, unlike malathion which kills any insect merely upon contact, even nontargeted species such as honeybees, the photoactive dye ingredient of the present invention is not harmful unless ingested. Indeed, the skin penetrability of phloxine B has been calculated to be about 87 times lower than that of malathion by octanol/water partition coefficient analysis conducted at the USDA.

Furthermore, because the active xanthene dye component is light-activated, a much smaller quantity is necessary to provide the desired effect. Moreover, contrary to the prior art broad spectrum pesticides which have a half-life on the order of months or even years, the xanthene based ingredient will naturally photodegrade in the environment within hours or, at the most, days. Thus, not only provide an extremely high kill rate when introduced in the targeted Mediterranean or oriental fruit fly populations, but additionally pose little or no risk for use in the agriculture industry.

An additional benefit which is offered by the use of xanthene based dyes as the active ingredient in pesticide compositions, resides in the fact that, after ingestion, the dye does not kill the insect immediately. This allows the insect which has ingested the pesticide to effectively transfer some quantity of the pesticide among other insects in the population. Therefore, substantially more insects will be eliminated due to the transfer of the toxic material between flies.

Another aspect of the invention is use of phloxine B in combination with uranine. Uranine is registered as D & C Yellow Dye No. 8 for use as a color additive in drugs and cosmetics.

The present insecticidal composition further contemplates the inclusion of an attractant bait which has the following properties: it attracts the target fruit flies to the location of the bait, and it stimulates the target fruit flies to feed on the bait. Attractant baits include (1) a carbohydrate sugar source, for example, sugars such as sucrose or fructose, or sugar substrates such as molasses or honey; (2) a proteinaceous food bait such as hydrolyzed protein (either by acid hydrolysis or enzymatic action), or (3) a combination of carbohydrate sugar source and hydrolyzed protein bait. The composition may optionally include anti-foaming agents and other adjuvants to increase the permeability of the ingested dye within the gut of the insect.

It is therefore an important object of the present invention to provide a pesticide that is toxic only when ingested by particular species of insects and in particular the Mediterranean or oriental fruit fly and other tephritid fruit flies.

It is a further object to provide a pesticide that has a delayed toxicity to the insect.

A still further object lies in the provisions of a pesticide which has minimal detrimental effect on the behavior of the insect between the period of ingestion and the onset of toxicity.

A still further object of the present invention lies in the provision of an insecticidal composition which is highly attractive to both sexes of the Mediterranean and oriental fruit fly.

A yet further object of the present invention resides in the provision of an insecticidal composition which contains no feeding inhibitors that may limit feeding or may induce a learned behavior to avoid the bait.

Lastly, it is an object of the present invention to provide an insecticidal composition which incorporates a bait that stimulates feeding and induces engorgement by the insects.

These together with other objects of the invention, are pointed out with particularity in the following detailed description and claims annexed hereto and forming part of this disclosure.

DETAILED DESCRIPTION OF THE INVENTION

Figure 1:
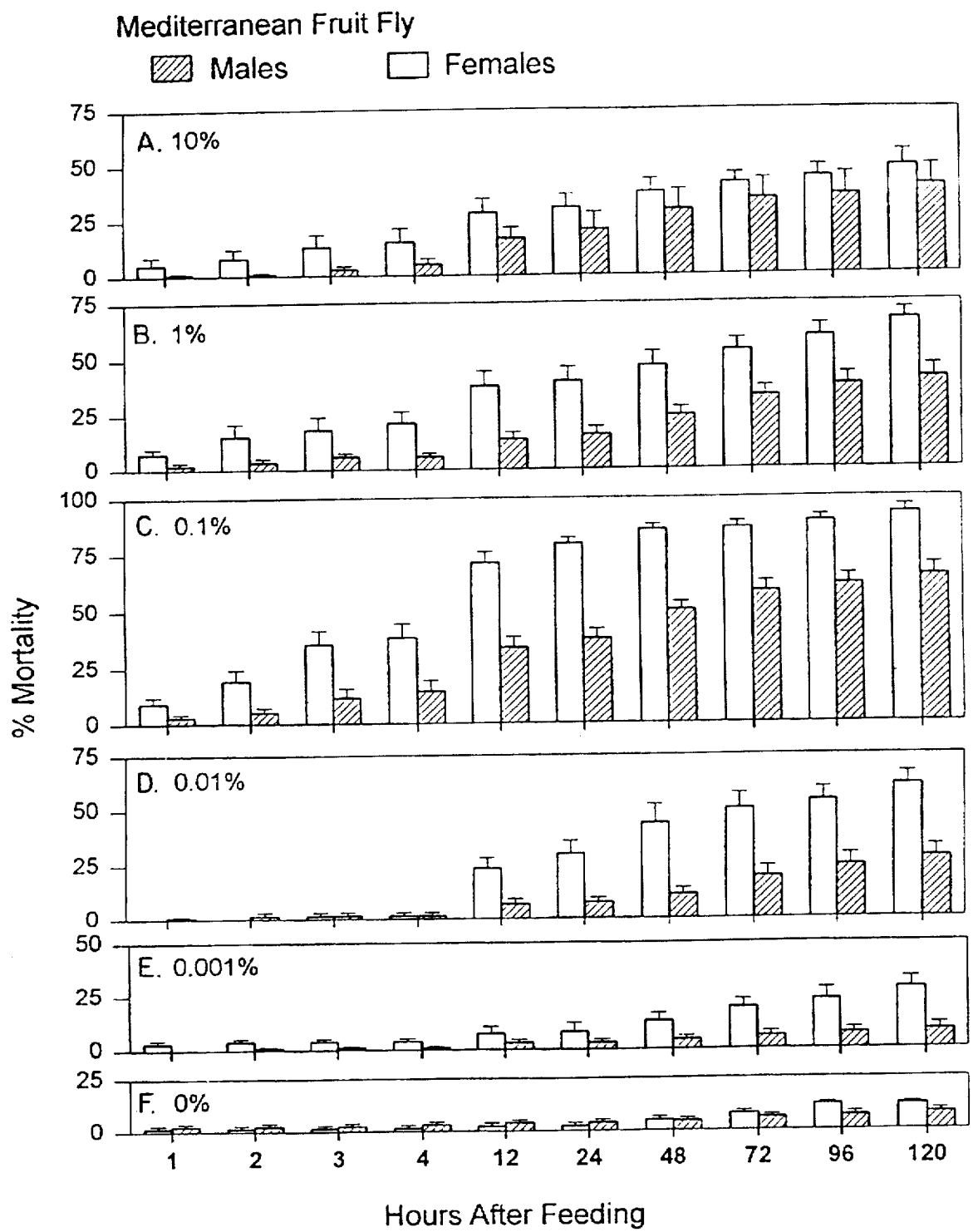
FIG. 1 shows percent mortality of adult Mediterranean fruit flies as a function of varying concentrations of 1:1 molar mixture of phloxine B and uranine and time after feeding.

Toxicity of several substituted xanthene dyes to many species of insects has been documented in the laboratory and field (Heitz, Chapter 1, *Light Activated Pesticides*, J. R. Heitz and K. R. Downum (eds.), American Chemical Society Symposium Series 339, American Chemical Society, Washington, D.C., 1987). Among these are the dye-sensitized photoactive toxicity of phloxine B to adult housefly, *Musca domestica* L. (Fondren and Heitz, *Environmental Entomology* 8:432–436, 1979), face fly, *M. autumnalis* De Geer (Fondren and Heitz, *Environmental Entomology* 7:843–846, 1978), boll weevil, *Anthonomus grandis* Boheman (Callaham et al., *Environmental Entomology* 4:837–841, 1975), black cutworm, *Agrotis ipsilon* (Clement et al., *Journal of Economic Entomology* 73:390–392, 1980), and imported fire ant, *Solenopsis richteri* (Forel) (Callaham et al., *Comp. Biochem. Physiol.* 51:123–128, 1975; Broome et al., *Environmental Entomology* 4:883–886, 1975). Light activated toxicity has also been reported in uranine-fed adult house fly (Fondren and Heitz, 1979, supra), face fly (Fondren and Heitz, 1978, supra), and imported fire ant (Callaham et al., 1975, supra). Although dye-sensitized photooxidative toxicity from uranine is considerably less than phloxine B, uranine has been found to cause synergistic effects when combined with other xanthene dyes. Phloxine B (2',4',5',7'-tetrabromo-4,5,6,7-tetrachlorofluorescein) is registered for use as a color additive in drugs and cosmetics. Uranine, chemically known as fluorescein 3',6'-dihydroxyspiro[isobenzofuran-1(3H,9'-[9H]xanthen]-3-one, disodium salt, is registered for use as a color additive in cosmetics as D & C Yellow No. 8.

The toxicity of phloxine B combined with uranine is of importance in finding suitable alternatives to insecticides that are mixed with food baits in sprays that are used in eradication or suppressing many tephritid fruit fly populations. Thus, in an effort to find an environmentally acceptable alternative to malathion, we determined the toxicity of a mixture of phloxine B and uranine to Mediterranean fruit fly and oriental fruit fly adults. Data presented here are fundamental information in developing bait formulations, containing phloxine B and uranine for controlling Mediterranean fruit fly and other tephritid fruit fly pests.

As discussed above, it is contemplated that the present insecticidal composition includes an attractant bait which attracts the target insect and stimulates it to feed on the bait. Attractant baits include 1) a carbohydrate sugar source, for example, sugars such as sucrose or fructose or complex sugar substrates such as molasses or honey; 2) a proteinaceous food bait such as hydrolyzed protein (either by acid hydrolysis or enzymatic action); 3) a combination of sugar source and hydrolyzed protein bait or 4) methyl eugenol.

Examples of hydrolyzed protein sources are the commercially available preparation, Nu-Lure™ (44% corn gluten meal, hydrolyzed, and 56% inert ingredients, Miller Chemical and Fertilizer, Hanover, Pa.), Mazoferm™ (condensed fermented corn extractives, E802, Corn Products, Summit-Argo, Ill.); hydrolyzed torula yeast, and hydrolyzed brewers yeast.

The dye and bait formulation can be used in dispensers set out in feeding bait stations or used in a sprayable formulation for ground or air applications. The formulation may be applied by various types of equipment from hand held sprayers to high pressure ground sprayers to helicopters to fixed-wing aircraft.

To accommodate for the different spray volume delivery rates, varying amounts of water is used as a diluent to the active ingredients of the spray formulation. An exemplary formulation is:

| | |
|---|---|
| photodye | from 0.1 to 1% of total formulation |
| hydrolyzed protein | from 35.0 to 99.0% of total formulation |
| sugar source | from 0.0 to 20% of total formulation |
| added water | from 0.0 to 70% of total formulation |

The total formulation should be applied so as to obtain good spray coverage with from 0.5 to 2.0 pounds of hydrolyzed protein per treated acre.

Another exemplary formulation is:

| photodye | from 0.1 to 1% of total formulation |
|---|---|
| sugar source | from 5 to 20% in water |

A dye plus bait formulation using methyl eugenol as the attractant bait is suitable for control of oriental fruit flies in male annihilation eradication programs. Male annihilation treatments are most often applied as spot applications of paste-like globs (generally about 600 spot applications per square mile) or as solutions adsorbed into solid carriers such as cigarette filter tips or 5 cm square fiberboard blocks hung on trees at rates of 500 to several thousand per square mile.

As known to those in the art, any specific methyl eugenol formulation and use pattern is chosen based on various factors including accessibility and/or whether it is applied in an inhabited area.

An exemplary formulation is:

| photodye | from 0.5 to 5.0% of total formulation by wt. |
|---|---|
| methyl eugenol | from 79.5 to 70.0% of total formulation |
| Min-U-Gel 400 (attapugite clay) | from 20 to 25% of total formulation |

The total formulation is applied as about 10 to 15 gram globs on tree trunks, telephone poles, etc. at a rate of about 600 spots per square mile about every two weeks. It can also be applied as a thickened spray by aircraft at a rate of about 20 lbs per square mile every 1 to 2 weeks.

Another exemplary formulation is:

| photodye | from 0.5 to 10.0% of total formulation by wt. |
|---|---|
| methyl eugenol | from 99.5 to 90.0% of total formulation |

This liquid formulation is adsorbed into various solid carriers such as cotton strings or wicks, cigarette filter tips, or cellulosic fiber wallboard cut into pieces of various sizes. These saturated solid carrier pieces can be distributed by aircraft or hung on foliage at a rate so that the total amount of liquid formulation is from about 20 to 100 lbs per square mile. Generally, applications are repeated every 2 to 8 weeks.

This liquid formulation can also be sprayed without any thickener or solid carrier at rates of 20 lbs per square mile in aerial applications at about weekly intervals.

The following examples describe the various innovative aspects of the present invention.

Materials and Methods

Insects:

Mediterranean fruit fly pupae and Oriental fruit fly pupae were obtained from the mass rearing facility of the USDA-ARS, Honolulu. Pupae were kept in an insectary at 75±5 degrees C., 60–75% relative humidity, and a 12:12 h (L.D.) photoperiod. Test adults were held under the same temperature, relative humidity, and photoperiod as the pupae, and were fed with water (in agar, consisting of 9.975 part water and 0.025 part agar (Gelcarin™) and diet consisting of 3 parts sucrose, 1 part protein yeast hydrolysate and 0.5 part Torula yeast. Five-d old adults were used in the succeeding experiments.

Example 1

Determining Variation in Mediterranean Fruit Fly Adult Mortality due to Concentration of Dyes, Sex, and Time after Feeding. Phloxine B and Uranine Mixed in 10% Molasses.

Five dilutions (percentage by weight) consisting of 0.001%, 0.01%, 0.1%, 1.0% and 10.0% of 1:1 molar mixture of phloxine B (829 g per mole) and uranine (376 g per mole) in a stock of 10% molasses were prepared. Test adult flies confined in feeding chambers were provided with dye-molasses preparations saturated in cotton wicks; control flies were provided with 10% molasses. Each feeding chamber had either 20 males or 20 females. Adult feeding with dye-molasses mixtures commenced at 06.00 h and terminated at 08:00 h, providing a 2-h feeding duration. From the onset of feeding, each feeding chamber was kept 10 cm below two high intensity, cool fluorescent lights yielding surface intensity of 18,000 LUX; the same lighting condition was maintained throughout the 12-h light phase of the experiment duration. Following removal of wicks containing the dyes, flies were provided with water and a diet consisting of sucrose, protein hydrolysate, and torula yeast. Mortality counts were made every hour for the first 4 hours following feeding, at 18:00 h when lights were automatically turned off, and during each succeeding morning at 8:00 h for 5 d. The experiment followed a randomized complete block design with 7 replicates. Adults used in the experiments were provided with only water 24 h (i.e., 12-h dark and 12-h lights periods) prior to their use in the experiment.

Results

FIG. 1 shows the Variation in Mediterranean fruit fly adult mortality due to concentration of dyes, sex and time after feeding. Phloxine B and Uranine were mixed in 10% Molasses. Mortality of Mediterranean fruit fly adults fed with various concentrations (by weight) of 1:1 molar mixture of phloxine B and uranine differed significantly with dose, sex, and number of hours after termination of feeding. Mortality of both males and females increased with the increase in concentration of dyes from 0.001% to 0.1%; however, at 1% to 10% concentrations, adult mortality was lower than that observed at 0.1%. Five days after feeding molasses with phloxine B and uranine, the trend in mortality by dose for males was 0.1%>0.01%=1%=10%>0.001%=0%; for females, the mortality trend was 0.1% >0.01%= 1%>10%>0.001%>0%. The cumulative mortality of females was higher than that of males for all concentrations, except at 10%. There was no significant increase in mortality 24 h after feeding on molasses with dyes for females and after 48 hours for males.

Example 2

Determining Functional Relationship Between Concentration of Dyes and Mortality of Mediterranean Fruit Fly Adults. Phloxine B and Uranium Mixed in 10% Molasses. Based on results obtained in study 1, concentration-mortality relationship was determined using the following molarity (M) concentrations of 1:1 molar mixture of phloxine B and uranine in 10% molasses: $2.5 \times 10^{-5}$, $5 \times 10^{-5}$, $1 \times 10^{-4}$, $2 \times 10^{-4}$, $4 \times 10^{-4}$, $8 \times 10^{-4}$, $1.6 \times 10^{-3}$, $3.2 \times 10^{-3}$, $6.4 \times 10^{-3}$, and $1.28 \times 10^{-2}$. The assay procedure was similar to the methodology described above. Control flies were fed with 10% molasses. Based on results of study 1, mortality counts were done only up to 2 d. Twenty groups of 20 flies (by sex) were tested for each dye concentration. Adults used in the test were not starved (i.e., 24 h prior to their use in the experiment, adults had sugar-protein-water diet during the 12 h light phase and were provided with water only during the (12 h dark phase).

Results

Figure 2:
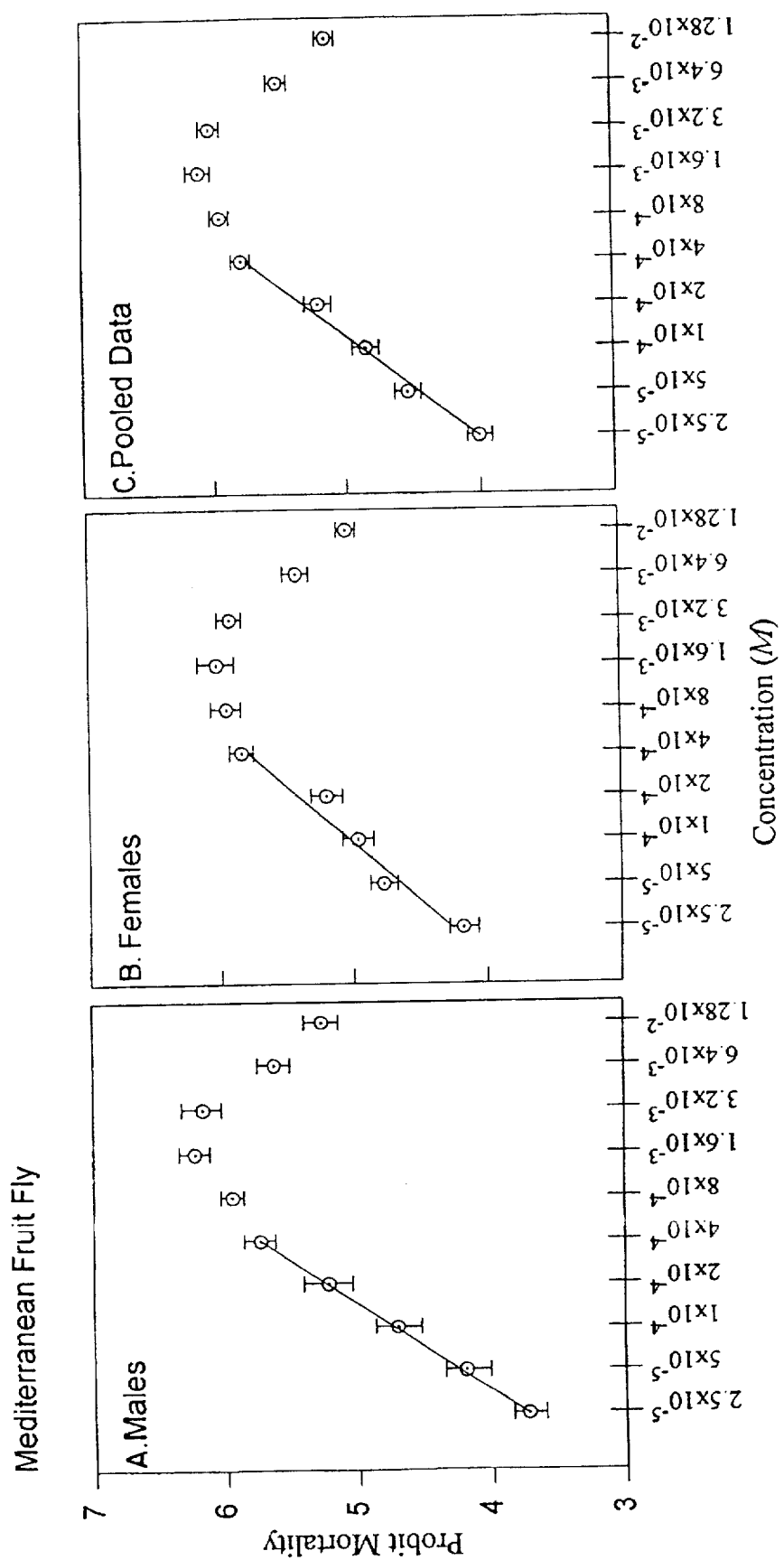
FIG. 2 shows the functional relationship between concentration of dyes in 10% molasses and mortality of Mediterranean fruit fly adults.

FIG. 2 shows the functional relationship between concentration of dyes and mortality. Phloxine B and uranine were in 10% molasses. Mortality of both males and females increased with the increase in concentration of dyes from $2.5\times10^{-5}$M to $1.6\times10^{-3}$M; however, at $3.2\times10^{-3}$M to $1.28\times10^{-2}$M, adult mortality was lower that that observed at $1.6\times10^{-2}$M. The $LC_{50}$ was $1.7\times10^{-3}$M for males and $1.3\times10^{-3}$M for females. Both sexes were deterred from feeding at concentrations greater than $1.6\times10^{-3}$M. The $LT_{50}$ at $1.6\times10^{-3}$M was about 7 hours for both sexes.

Example 3

Phloxine B and Uranine Mixed in 1% NuLure. Various dilutions of dyes were prepared in a stock of 1% NuLure (a commercial hydrolyzed protein bait preparation) 44% corn gluten meal, hydrolyzed and 56% inert ingredients, Miller. Concentration mortality relationship was determined using the following molarity (M) concentrations: $2.5\times10^{-5}$, $1\times10^{-4}$, $4\times10^{-4}$, $8\times10^{-4}$, $1.6\times10^{-3}$. Control flies were fed with 1% NuLure. The assay procedure was similar to the method described above, except that fourteen groups of 20 females were tested for each dye concentration. Test adults were not starved (i.e. 24 h prior to their use in the experiment, adults had sugar-protein-water diet during the 12 h light phase and were provided with water only during the 12 h dark phase).

Results

Figure 3:
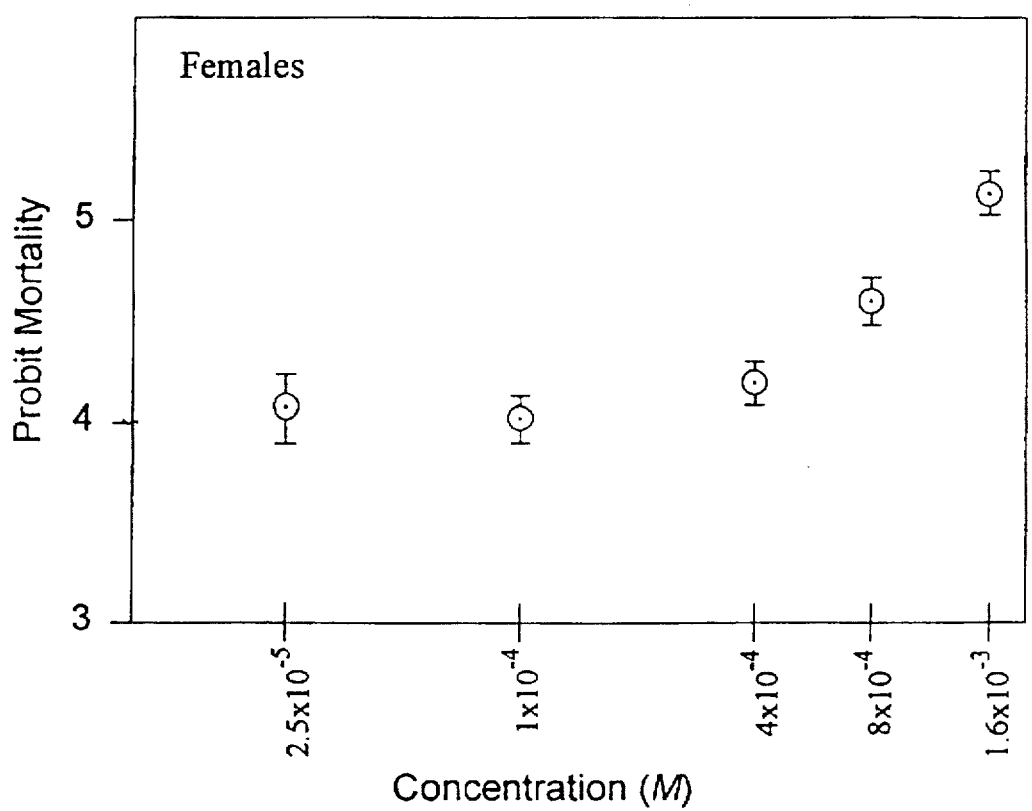
FIG. 3 shows the functional relationship between concentration of dyes in 1% Nu-Lure and mortality of Mediterranean fruit fly adults.

FIG. 3 shows that when the food carrier for dye was 1% NuLure (i.e., with relatively much lower feeding stimulant than molasses), there was no significant increase in mortality from $2.5\times10^{-5}$ to $4\times10^{-4}$ significant increase in mortality was observed from $4\times10^{-4}$ to $1.6\times10^{-3}$. The $LC_{50}$ was $1.6\times10^{-3}$M for females. However, the $LT_{50}$ at $1.6\times10^{-3}$M was about 35 h. Combined results shown in FIGS. 2 & 3 emphasize the importance of food carrier in the adult feeding consumption and consequently the level of mortality due to the light-activated dye toxicity.

Our data attest to the insecticidal activity of Phloxine B and Uranine mixture to Mediterranean fruit fly adults and provide fundamental information for developing phloxine B+uranine+bait formulations for large-scale, area-scale, area-wide spray applications.

The ratio and absolute amounts of the photodye, attractant bait in commercial formulations may vary and may be readily predetermined by the practitioner skilled in the art by routine testing. It will be recognized that the photodye should be employed in an amount effective to result in a significant growth inhibition or mortality rate of a test group of the target insect as compared to an untreated group. Furthermore, the amount of attractant bait employed should be effective to attract the target insect and stimulate it to feed on the bait. The actual effective amounts of the photodye and attractant bait may vary with environmental conditions such as temperature, humidity and wind, the type of vehicle or carrier employed, application protocol, and stage of target insect development.

Example 4

Determining Functional Relationship Between Concentration of Dyes and Mortality of Oriental Fruit Fly Adults. Phloxine B and Uranine Mixed in 1% NuLure; Adult Provided With A Feeding Choice. Concentration-mortality relationship was determined using the following molarity (M) concentrations of 1:1 molar mixture B and uranine in 1% NuLure: $4\times10^{-4}$, $8\times10^{-4}$, $1.6\times10^{-3}$. The assay procedure was similar to the methodology described above. However, the test adults were provided with a feeding choice of two types of food: 2 wicks with only 1% NuLure and another 2 wicks with 1% NuLure mixed with dyes. Control flies were fed with 1% NuLure. Mortality counts were done up to 2 d. Three groups of 20 flies (by sex) were tested for each dye concentration. Adults used in the test were not starved (i.e., 24 h prior to their use in the experiment, adults had sugar-protein-water diet during the 12-h light phase and were provided with water only during the 12-h dark phase).

Figure 4:
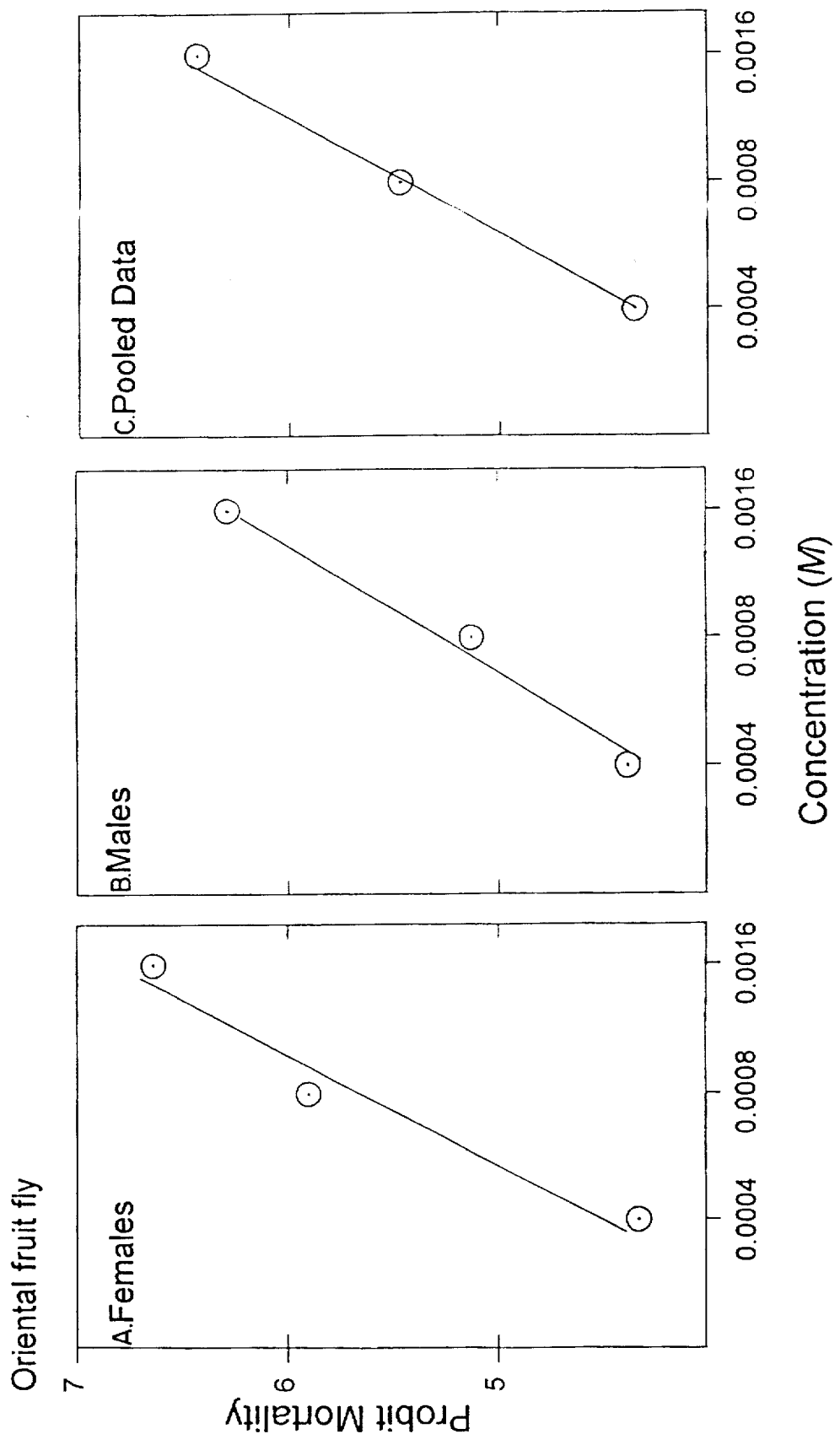
FIG. 4 shows the functional relationship between concentration (M) of 1:1 molar mixture of phloxine B and uranine in 1% Nu-Lure and mortality of oriental fruit fly adults.

Results (FIG. 4) show the high toxicity (>60%) of 1:1 molar mixture Phloxine B and uranine to Oriental fruit fly adults, even in the presence of a choice of food that do not contain the dyes.

Example 5

Hydrolyzed Protein Bait Sprays Containing Phloxine B and Uranine for Controlling Mediterranean Fruit Fly and Oriental Fruit Fly (Diptera: Tephritidae) Infestations. Insecticidal efficacy of Phloxine B and Uranine mixed in hydrolyzed protein bait sprays was assessed against an established, high density Mediterranean fruit fly population in coffee fields on Kauai, Hi. An experimental use permit from the State of Hi. allowed treatment of 10 acres amidst thousands of acres of productive coffee fields. A mixture of 2.2 oz of a 1:1 molar mixture of Phloxine B and Uranine, 16.23 fl oz of hydrolyzed protein bait (NuLure), and 15.5 gal of water was ground-sprayed for 20 applications over a 3 month period on 10 acres of coffee, while there was no spraying on an adjacent (control) 10 acres. Densities of Mediterranean fruit fly and oriental fruit fly adults were reduced by 50% in the treated field after the completion of the spraying program, with corresponding suppression of their level densities in coffee berries collected from the treated field. These results were significant because the thousand of acres surrounding the 10-acre treatment plot produced hundreds of thousands of adults fruit flies that were constantly immigrating into the treatment plot.

Example 6

Determining Variation in Oriental Fruit Fly Adult Mortality due to Concentration of Dyes, Sex, and Time after Feeding. Phloxine B and Uranine Mixed in Aqueous Solution containing 20% Yeast Hydrolysate and 20% Fructose. Eleven concentrations, consisting of $1.25\times10^{-5}$M, $2.5\times10^{-5}$M, $5.0\times10^{-5}$M, $1.0\times10^{-4}$M, $2.0\times10^{-4}$M, $4.0\times10^{-4}$M, $8.0\times10^{-4}$M, $1.6\times10^{-3}$M, $3.2\times10^{-3}$M, $6.4\times10^{-3}$M, and $1.28\times10^{-2}$M of 1:1 molar mixture of phloxine B (829 g per mole) and uranine (376 g per mole) were prepared in a stock of 20% yeast hydrolysate and 20% fructose. Six-d old adult flies confined in feeding chambers were provided with the treatment solutions saturated in cotton wicks; control flies were provided with the stock solution. Each feeding chamber had either 20 males or 20 females. Adult feeding with dye-stock mixtures commenced at 08:00 h and terminated at 12:00 h, providing a 4-h feeding duration. At the onset of feeding each feeding chamber was kept 10 cm below two high intensity, cool fluorescent lights covered with an 80% shade cloth yielding surface light intensity of 600 lux. Following the feeding period, the shade cloth was removed and two additional fluorescent tubes were turned on, resulting in a light intensity of 18,000 lux which was then maintained throughout the remaining 12-h light phase of the experiment. Upon removal of the wicks containing the treatment solutions, flies were provided with water and a diet consisting of sucrose, protein hydrolysate, and torula yeast. Mortality counts were made at the time wicks were removed and 2 h, 4 h, 6 h, 24 h, and 48 h later. The experiment followed a randomized complete block design with 7 replicates per sex-treatment combination.

Results

Figure 5A:
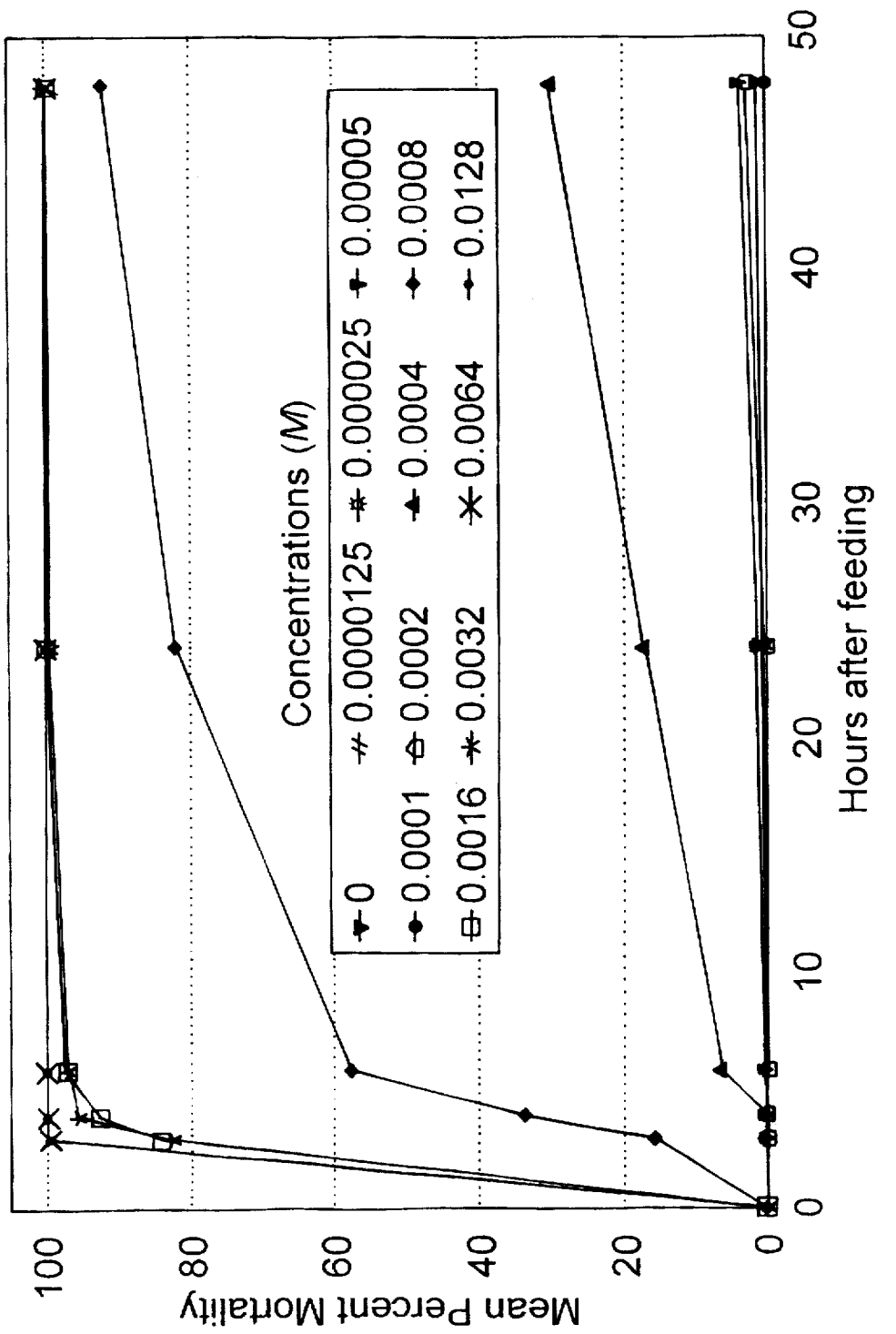
FIGS. 5A and 5B show percent mortality of adult oriental fruit fly males and females, respectively, as a function of varying concentrations of 1:1 molar mixture of phloxine B and uranine and time after feeding.
Figure 5B:
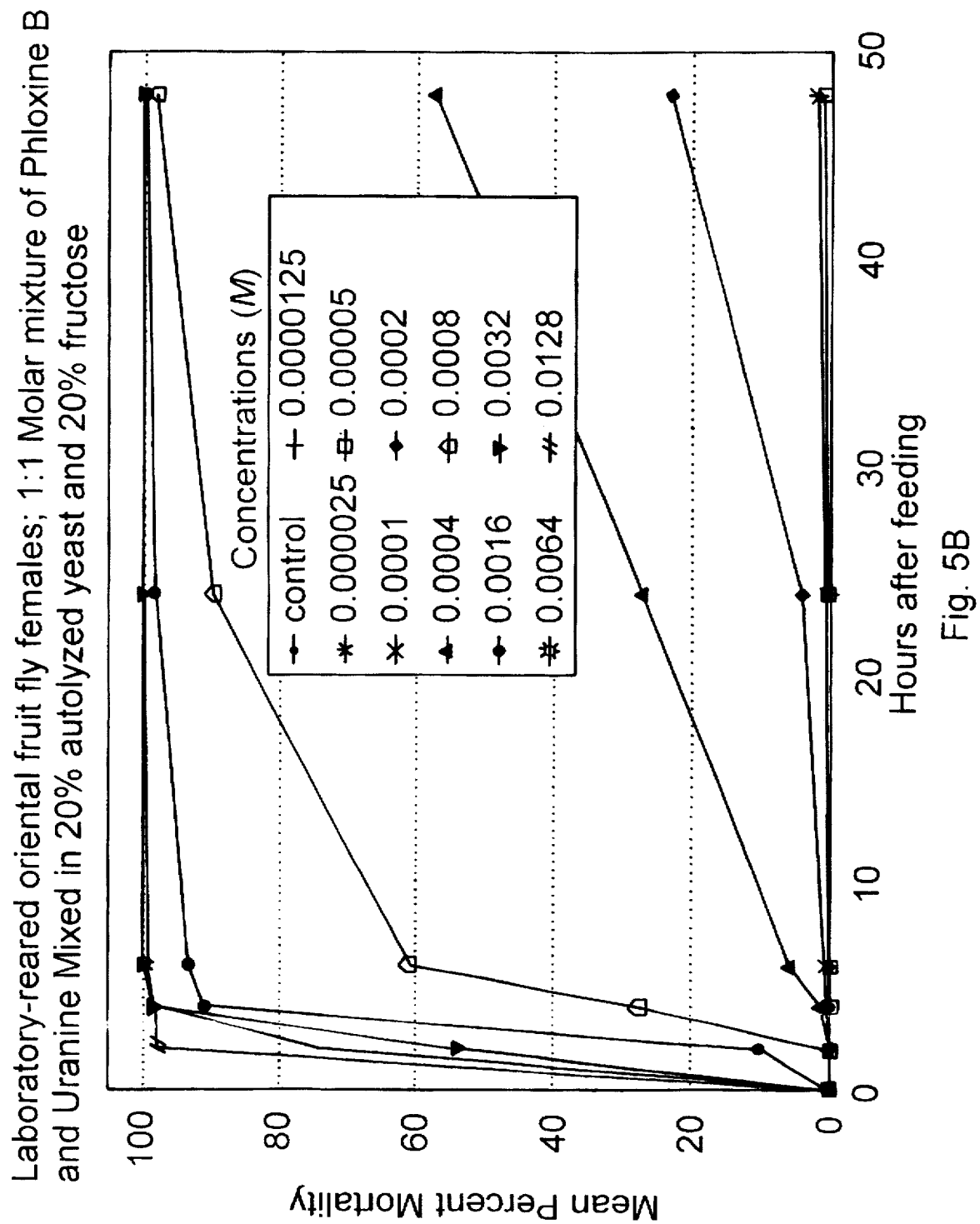

FIGS. 5A and 5B show the variation in oriental fruit fly adult mortality due to concentration of dyes and time after feeding for males and females, respectively. Mortality of oriental fruit fly adults differed with dose and number of hours after termination of feeding, but was similar for males and females. Rate of kill increased with increasing concentration, with 100% mortality achieved after 2 h of light exposure at high dye concentrations ($6.4 \times 10^{-3}$M and $1.28 \times 10^{-2}$M). Concentrations less than or equal to $1.0 \times 10^{-4}$ failed to increase mortality beyond control levels.

Example 7

Determining Relative Mortality of Oriental Fruit Flies when Exposed to Dye Mixed with Methyl Eugenol as compared to Methyl Eugenol alone or Methyl Eugenol+dog collar (i.e., source of the insecticide Naled). Containers with 4–2.5 cm diameter openings on the sides and holding a 2.5 cm long cotton wick holding 1.0 ml of either methyl eugenol alone (treatments 1 and 2) or a $1.28 \times 10^{-2}$M concentration of Phloxine B+Uranine in methyl eugenol (treatment 3) were set out in an orchard, with supplemental release of irradiated oriental fruit flies. Treatment 2, additionally, had a strip of dog collar added to the interior of the container as a knock-down toxicant. One and one-half hours after the fly release, containers were collected with screen added to the openings to trap all contained flies. Containers were then exposed to full daylight and mortality counts were taken every half hour for the next two hours, after which the total number of flies was counted in each chamber. The experiment followed a randomized complete block design with 5 replicates per treatment.

Results

Figure 6:
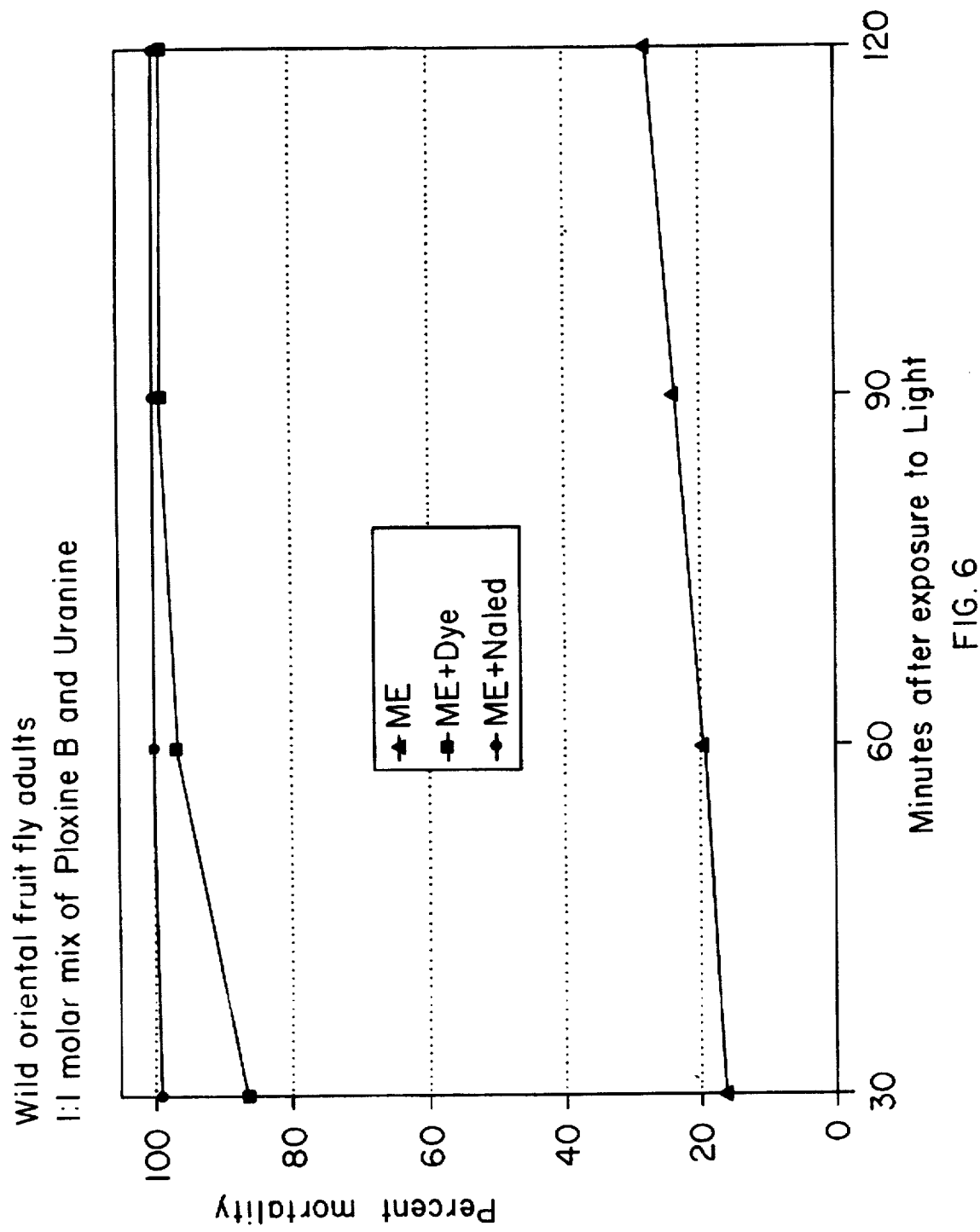
FIG. 6 shows percent mortality of wild oriental fruit fly adults as a function of methyl eugenol alone, methyl eugenol plus a 1:1 molar mixture of phloxine B and uranine, and methyl eugenol plus naled, and time after exposure to light.

FIG. 6 shows the average mortality in the three treatments over time. There was a high initial rate of mortality in the treatment including the dog collar strip. Two hours after exposure to full sunlight, there was greater than 98% mortality in containers to which dye had been added to the methyl eugenol wicks, compared to 100% mortality in containers which had a strip of dog collar and less than 25% mortality in chambers with only methyl eugenol contained in the wicks.

Example 8

Determining Whether Increase of Dye Concentration in Methyl Eugenol above $1.28 \times 10^{-2}$M Improves the Rate of Kill of Oriental Fruit Flies. Containers with 4–2.5 cm diameter openings on the sides and holding a 1.8 cm long cotton wick holding 1.0 ml of either methyl eugenol alone (treatments 1 and 2) or a $1.28 \times 10^{-2}$M (treatment 3) or $4.29 \times 10^{-2}$M (treatment 4) concentration of Phloxine B+Uranine in methyl eugenol were set out in a citrus orchard known to have a wild population of oriental fruit flies. After two hours traps were recovered with screens added to the holes to entrap any contained flies. Wicks In treatment numbers 2–4 were replaced with water saturated wicks while wicks in treatment number 1 were not exchanged or removed. Containers were moved to full daylight and mortality counts were taken periodically over the next two hours, after which the total number of flies was counted in each container, and the number of live flies with reddened abdomens in the containers which had included dye in their initial wicks. The experiment followed a randomized complete block design with 3 replicates per treatment.

Results

Figure 7:
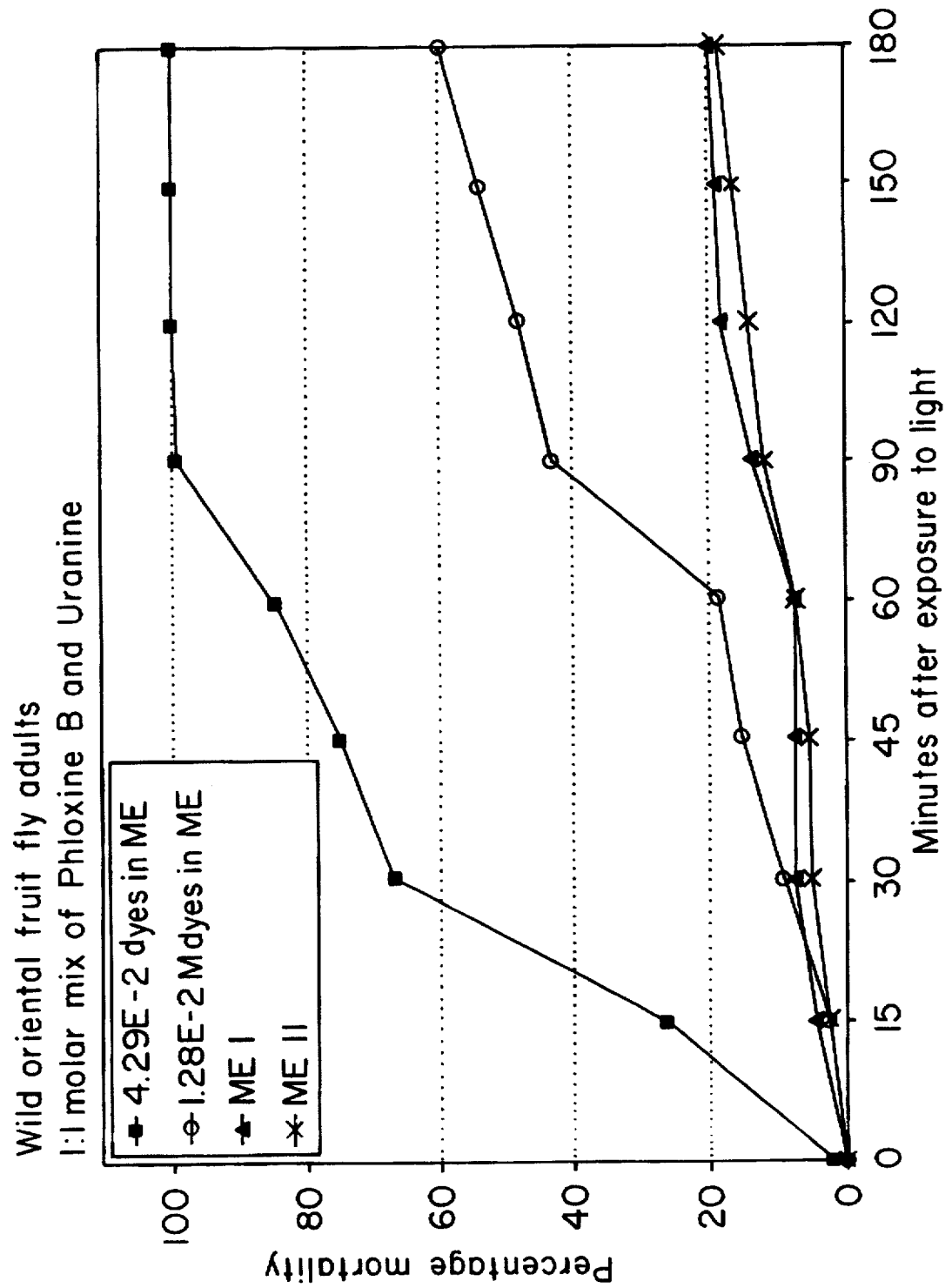
FIG. 7 shows the increase in mortality over time of wild oriental fruit fly adults exposed to methyl eugenol alone and methyl eugenol plus a 1:1 molar mixture of phloxine B and uranine at two concentrations.

FIG. 7 shows the increase in mortality over time in the 4 treatments. By 30 minutes after the exposure of the chambers to full daylight, over 66% of the flies in the $4.29 \times 10^{-2}$M dye treatment containers had died compared to less than 10% of those in the $1.28 \times 10^{-2}$M dye treatment containers. By 2 hours these percentages had increased to 100% of the flies in the $4.29 \times 10^{-2}$M dye treatment containers and less than 50% of those in the $1.28 \times 10^{-2}$M dye treatment containers. None of the flies in the $1.28 \times 10^{-2}$M dye treatment containers which continued to survive at the end of the experiment had reddened abdomens. Average mortalities in the two methyl eugenol only treatments were less than 8% and less than 20% at these two time periods, respectively.

Example 9

Determining Whether Phloxine B Alone (no Added Uranine $4.29 \times 10^{-2}$M and $8.58 \times 10^{-2}$M Concentrations) in Methyl Eugenol is Effective in Killing Oriental Fruit Fly Adults and Whether Rate of Kill is Greater with $8.58 \times 10^{-2}$M than $4.29 \times 10^{-2}$M. Containers with 4–2.5 cm diameter openings on the sides and holding a 1.8 cm long cotton wick holding 1.0 ml of either methyl eugenol alone (treatments 1 and 2) or a $4.29 \times 10^{-2}$M (treatment 3) or $8.58 \times 10^{-2}$M (treatment 4) concentration of Phloxine B (without the addition of Uranine) in methyl eugenol were set out in a citrus orchard known to have a wild population of oriental fruit flies. After two hours traps were recovered with screens added to the holes to entrap any contained flies. Wicks in treatment numbers 2–4 were replaced with water saturated wicks while wicks in treatment number 1 were not exchanged or removed. Containers were moved to full daylight and mortality counts were taken periodically over the next two hours, after which the total number of flies was counted in each container; during these 2-h period, the weather condition was overcast with intermittent rains. The experiment followed a randomized complete block design with 6 replicates per treatment.

Results

Figure 8:
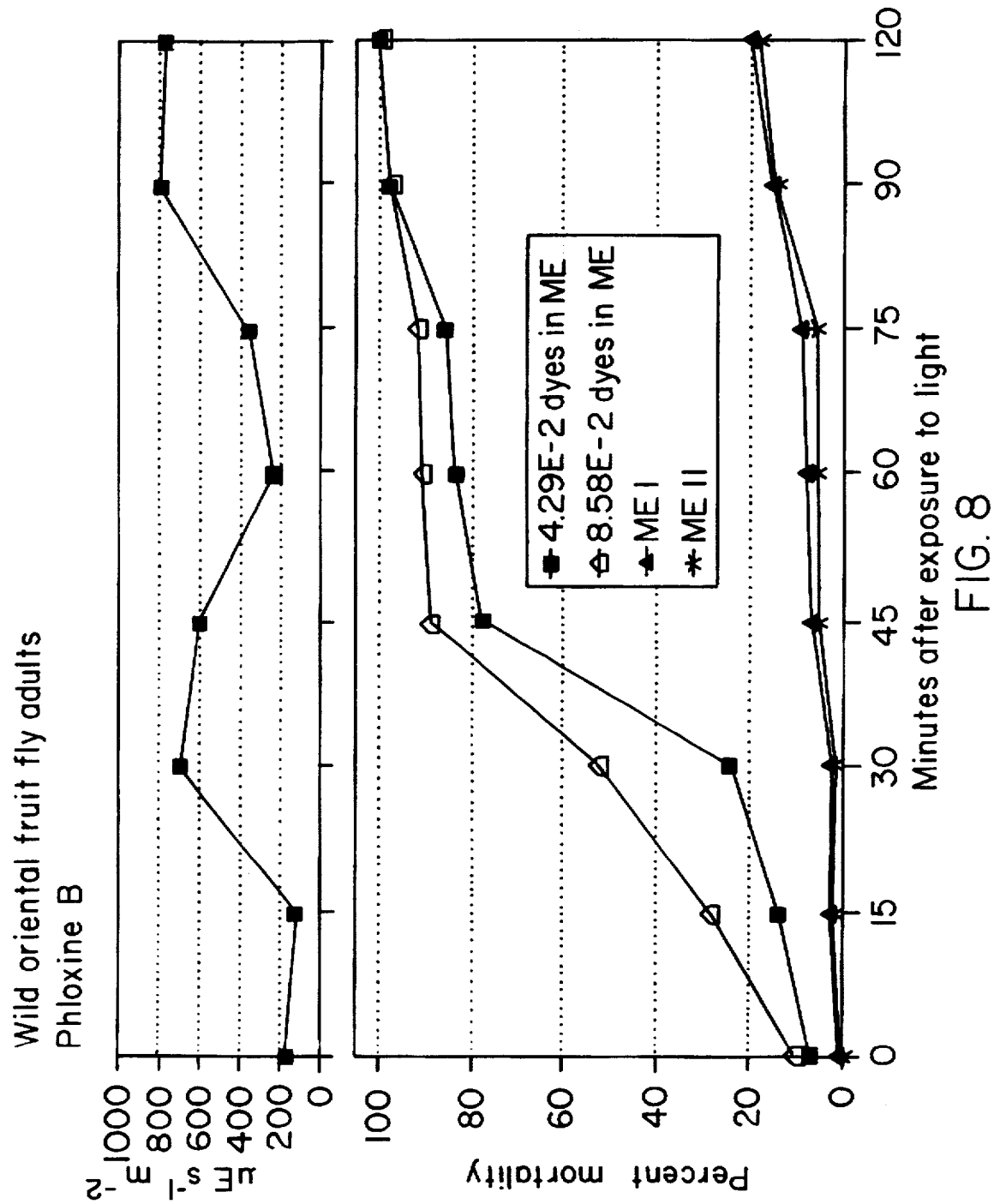
FIG. 8 shows the increase in mortality over time of wild oriental fruit fly adults exposed to methyl eugenol alone and methyl eugenol plus phloxine B at two concentrations.

FIG. 8 shows the increase in mortality over time in the 4 treatments. After 30 minutes of exposure to full daylight conditions, over 50% of the flies had died in the $8.58 \times 10^{-2}$M dye treatment while less than 25% had died in the $4.29 \times 10^{-2}$M dye treatment. Both control treatments averaged less than 3% mortality after 30 minutes. The difference in total mortality between the two dye treatments, however, became less over time, both reaching 100% after 2 hours of exposure, at which point both control treatments averaged less than 21% mortality.

What is claimed is:

1. An insecticidal composition comprising an effective amount of methyl eugenol as an attractant bait and an effective insecticidal amount of photoactive dye wherein said photoactive dye is selected from the group consisting of halogenated xanthene and a mixture of halogenated xanthene and uranine.

2. The composition of claim 1 which contains between about 0.001% to about 10.0% by weight of said photoactive dye and 90.0 to 99.5% of methyl eugenol.

3. A method for eradicating or suppressing a population of oriental fruit flies comprising applying to the habitat of said oriental fruit flies the composition of claim 1 and causing said composition to be ingested.

* * * * *

UNITED STATES PATENT AND TRADEMARK OFFICE
CERTIFICATE OF CORRECTION

PATENT NO. : 5,728,394
DATED : March 17, 1998
INVENTOR(S) : Liquido et al

It is certified that error appears in the above-identified patent and that said Letters Patent is hereby corrected as shown below:

On the title page : under item attorney, agent or firm portion of the patent should read:

Attorney, Agent or Firm: Leonard Bloom and M. Howard Silverstein, John D. Fado and Margaret A. Connor Column 7, line 2, "that" first occurrence should read --than--.

Column 7, lines 13 and 14 "1 x 10 $^-_4$" should read --$1 \times 10^{-4}$--.

Column 8, lines 34 and 35, "2.5 x 10$^-_5$M" should read --$2.5 \times 10^{-5}M$--.

Column 8, lines 36 and 37, "1.28 x 10$^-_2$M" should read --$1.28 \times 10^{-2}M$--.

Signed and Sealed this

Eighth Day of September, 1998

Attest:

BRUCE LEHMAN

*Attesting Officer*   *Commissioner of Patents and Trademarks*